US00PP26532P2

(12) United States Plant Patent
Warner

(10) Patent No.: US PP26,532 P2
(45) Date of Patent: Mar. 29, 2016

(54) SHRUB ROSE PLANT NAMED 'CHEWNICEBELL'

(50) Latin Name: *Rosa hybrida*
Varietal Denomination: Chewnicebell

(71) Applicant: Christopher H. Warner, Newport (GB)

(72) Inventor: Christopher H. Warner, Newport (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 186 days.

(21) Appl. No.: 13/998,235

(22) Filed: Oct. 11, 2013

(51) Int. Cl.
*A01H 5/02* (2006.01)

(52) U.S. Cl.
USPC ..... Plt./102

(58) Field of Classification Search
USPC ..... Plt./102, 130, 141, 103, 107
See application file for complete search history.

(56) References Cited

PUBLICATIONS

Garden Crossings Oso Easy Italian Ice Rosa 'ChewNiceBell' PPAF, retrieved on Jun. 9, 2015, retrieved from the Internet at <http://www.gardencrossings.com/plantname/Rose-Oso-Easy-Italian-Ice 2 pp.*
Winona Horticultural Society Newsletter Jan. 2013, retrieved on Jun. 9, 2015, retrieved from the Internet at <http://www.gardenontario.org/docs/2013_01_Winona_Newsletter.pdf> 4 pp.*
Plant Varietyis Journal Oct. 2012/No. 85, pp. 1-2 and 21.*

* cited by examiner

*Primary Examiner* — June Hwu
(74) *Attorney, Agent, or Firm* — C. A. Whealy

(57) ABSTRACT

A new and distinct cultivar of Rose plant named 'Chewnicebell', characterized by its upright, somewhat outwardly spreading and mounding plant habit; glossy green-colored leaves; freely branching growth habit; freely flowering habit; large light pink and yellow-colored flowers; resistance to Black Spot; and good garden performance.

1 Drawing Sheet

Botanical designation: *Rosa hybrida.*
Cultivar denomination: 'CHEWNICEBELL'.

BACKGROUND OF THE INVENTION

The present Invention relates to a new and distinct Rose plant, botanically known as *Rosa hybrida*, commercially used as an ornamental Shrub Rose and hereinafter referred to by the name 'Chewnicebell'.

The new Rose plant is a product of a planned breeding program conducted by the Inventor in Newport, Shropshire, United Kingdom. The objective of the breeding program was to develop new uniform and disease-resistant shrub Rose plants with large and attractive flowers.

The new Rose plant originated from a cross-pollination made by the Inventor in June, 1998 of *Rosa hybrida* 'Pandemonium', not patented, as the female, or seed, parent with *Rosa hybrida* 'Scrivbell', not patented, as the male, or pollen, parent. The new Rose plant was discovered and selected by the Inventor in 2004 as a single flowering plant within the progeny of the stated cross-pollination in a controlled environment in Newport, Shropshire, United Kingdom.

Asexual reproduction of the new Rose plant by softwood cuttings at Newport, Shropshire, United Kingdom since 2004 has shown that the unique features of this new Rose plant are stable and reproduced true to type in successive generations of asexual reproduction.

SUMMARY OF THE INVENTION

The following traits have been repeatedly observed and are determined to be the unique characteristics of 'Chewnicebell'. These characteristics in combination distinguish 'Chewnicebell' as a new and distinct Rose plant:

1. Upright, somewhat outwardly spreading and mounding plant habit.
2. Glossy green-colored leaves.
3. Freely branching growth habit.
4. Freely flowering habit.
5. Large light pink and yellow-colored flowers.
6. Resistant to Black Spot (*Diplocarpon rosae*).
7. Good garden performance.

Plants of the new Rose differ from plants of the female parent, 'Pandemonium', in the following characteristics:

1. Plants of the new Rose are not as fragrant as plants of 'Pandemonium'.
2. Plants of the new Rose and 'Pandemonium' differ in flower color as plants of 'Pandemonium' have striped orange and yellow-colored flowers.
3. Plants of the new Rose are more resistant to Black Spot than plants of 'Pandemonium'.

Plants of the new Rose differ from plants of the male parent, 'Scrivbell', in the following characteristics:

1. Flowers of plants of the new Rose have more petals than flowers of plants of 'Scrivbell'.
2. Flowers of plants of the new Rose are not as fragrant as flowers of plants of 'Scrivbell'.
3. Plants of the new Rose and 'Scrivbell' differ in flower color as plants of 'Scrivbell' have pink and white-colored flowers.
4. Plants of the new Rose are more resistant to Black Spot than plants of 'Scrivbell'.

Plants of the new Rose can be compared to plants of the *Rosa hybrida* 'Chewhocan', disclosed in U.S. Plant patent application Ser. No. 13/998,221. Plants of the new Rose differ primarily from plants of 'Chewhocan' in flower color as flowers of plants of 'Chewhocan' are clear yellow in color.

BRIEF DESCRIPTION OF THE PHOTOGRAPH

The accompanying colored photograph illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

The photograph comprises a top perspective view of a typical plant of 'Chewnicebell' grown in a container.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photograph, following observations and measurements describe plants grown in two-gallon containers during the summer in an outdoor nursery in Grand Haven, Mich. and under cultural practices typical of commercial Rose production. Plants were two years old when the photographs and description were taken. In the following description, color references are made to The Royal Horticultural Society Colour Chart, 1995 Edition, except where general terms of ordinary dictionary significance are used.

Botanical classification: *Rosa hybrida* 'Chewnicebell'.

Parentage:

*Female, or seed, parent.*—*Rosa hybrida* 'Pandemonium', not patented.

*Male, or pollen, parent.*—*Rosa hybrida* 'Scrivbell', not patented.

Propagation:

*Type*.—By softwood cuttings.

*Time to initiate roots*.—About 12 days at 25° C.

*Time to produce a rooted young plant*.—About three months at 25° C.

*Root description*.—Somewhat fibrous, fine to thick; white, close to 155A, to brown, close to 200B in color.

*Rooting habit*.—Freely branching; dense.

Plant description:

*Plant form*.—Upright, somewhat outwardly spreading and mounding perennial shrub.

*Growth habit*.—Vigorous growth habit; rapid growth rate.

*Branching habit*.—Freely branching habit; about 32 primary lateral branches develop per plant; dense and bushy growth habit; pinching enhances lateral branch development.

*Plant height*.—About 33 cm.

*Plant width* (*spread*).—About 52 cm.

*Lateral branches*.—Length: About 25 cm. Diameter: About 2 mm. Internode length: About 2.5 cm. Strength: Strong. Texture: Smooth, glabrous. Color: Close to 143A; developing stems, tinged with close to 53A; new growth in spring and full sunlight, close to 178A and 60A. Thorns: Density: About one to three thorns per node on a developed lateral branch. Shape: Triangular with sharp acuminate apices. Height: About 5 mm. Diameter, at base: About 5 mm. Color: Close to 184B.

Leaf description:

*Arrangement*.—Alternate; pinnately compound with about five to seven leaflets per leaf.

*Leaf length*.—About 10 cm.

*Leaf width*.—About 7 cm.

*Leaflet length*.—About 3.5 cm.

*Leaflet width*.—About 2.2 cm.

*Leaflet shape*.—Ovate.

*Leaflet apex*.—Acute.

*Leaflet base*.—Obtuse.

*Leaflet margin*.—Serrate.

*Leaflet texture, upper and lower surfaces*.—Smooth, glabrous.

*Leaflet luster, upper and lower surfaces*.—Glossy.

*Leaflet venation pattern*.—Pinnate.

*Leaflet color*.—Developing leaflets, upper surface: Close to 137A. Developing leaflets, lower surface: Close to 147B. Fully expanded leaflets, upper surface: Close to 137A; venation, close to 136A. Fully expanded leaflets, lower surface: Close to 137B; venation, close to 183A.

*Leaf petiole*.—Length: About 1.5 cm. Diameter: About 2 mm. Texture, upper and lower surfaces: Smooth, glabrous. Color, upper and lower surfaces: Close to 144A.

*Stipules*.—Length: About 8 mm to 10 mm. Width: About 2 mm. Shape: Winged with an acute apex. Texture, upper and lower surfaces: Smooth, glabrous. Color: Close to 144C.

Flower description:

*Flower type and habit*.—Rotate rounded flowers arranged singly or in umbel-like clusters of two to three; flowers face mostly upright or outwardly; freely flowering with plants developing about 160 flowers during the flowering period.

*Natural flowering season*.—Plants flower continuously in the landscape during the summer in Grand Haven, Mich.; during this period flowering is continuous; flowers persistent.

*Fragrance*.—Moderately fragrant; sweet, pleasant.

*Flower buds*.—Height: About 1.3 cm. Diameter: About 1 cm. Shape: Ovoid. Texture: Rugose, glabrous. Color: Close to 13B.

*Flower diameter*.—About 6.5 cm.

*Flower depth*.—About 2.5 cm.

*Petals*.—Quantity per flower: About 16 in several whorls. Length: About 3 cm. Width: About 2.6 cm. Shape: Obovate. Apex: Obtuse; moderately to weakly reflexing. Base: Attenuate. Margin: Entire; undulate. Texture, upper and lower surfaces: Smooth, glabrous. Color: Developing and fully expanded petals, upper surface: Close to 6C flushed with close to 69A and 68D; towards the base, close to 6C and 6D; with development, color becoming closer to 6D flushed with close to 69A. Developing and fully expanded petals, lower surface: Close to 6D; towards the base, close to 6C; towards the apex, flushed with close to 69A.

*Sepals*.—Quantity per flower: Five. Length: About 2.3 cm. Width: About 1.1 cm. Shape: Subulate. Apex: Acuminate. Base: Obtuse. Margin: Dentate; no foliaceous extensions observed. Texture, upper and lower surfaces: Smooth, glabrous. Color: Developing and fully expanded sepals, upper surface: Close to 143C. Developing and fully expanded sepals, lower surface: Close to 138B.

*Peduncles*.—Length: About 4 cm. Diameter: About 5 mm. Orientation: Erect to about 10° from vertical. Strength: Strong. Color: Close to 143C.

*Reproductive organs*.—Stamens: Quantity per flower: Numerous, about 53. Anther shape: Round. Anther length: About 1 mm. Anther color: Close to 53A. Pollen amount: Moderate. Pollen color: Close to 4D. Pistils: Quantity per flower: About 17. Pistil length: About 1.6 cm. Stigma shape: Round. Stigma color: Close to 22B. Style length: About 4 mm. Style color: Close to 50B. Ovary color: Close to 138A.

*Fruits*.—Diameter: About 1 cm to 1.2 cm. Shape: Globular. Color: Close to 144A; with frost, color becoming closer to 200A.

*Seeds*.—Diameter: About 1 mm to 2 mm. Shape: Roughly tear-shaped. Color: Close to 160B.

Pathogen & pest resistance: Plants of the new Rose have been observed to be resistant to Black Spot (*Diplocarpon rosae*). Plants of the new Rose have not been observed to be resistant to pests and other pathogens common to Rose plants.

Garden performance: Plants of the new Rose have been observed have good garden performance and to tolerate rain, wind and temperatures ranging from about −25° C. to about 30° C.

It is claimed:

1. A new and distinct Rose plant named 'Chewnicebell' as illustrated and described.

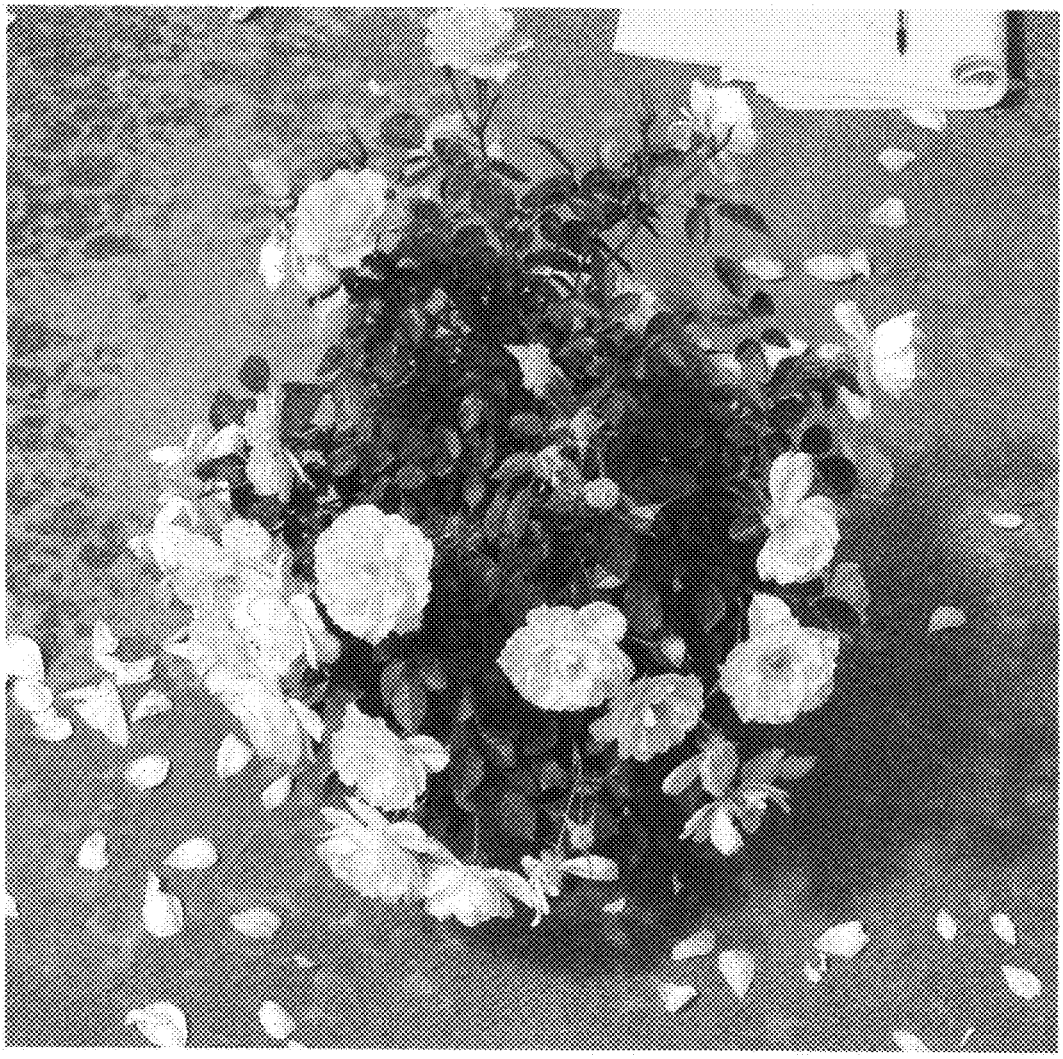

* * * * *